United States Patent [19]

Miller

[11] Patent Number: 5,731,506
[45] Date of Patent: Mar. 24, 1998

[54] INBRED CORN LINE CG00766

[75] Inventor: Robert L. Miller, Cedar Rapids, Iowa

[73] Assignee: Novartis Corporation

[21] Appl. No.: 729,889

[22] Filed: Oct. 15, 1996

Related U.S. Application Data

[63] Continuation of Ser. No. 391,906, Feb. 21, 1995, abandoned.
[51] Int. Cl.[6] ............................. A01H 5/00; A01H 4/00; C12N 5/04
[52] U.S. Cl. ..................... 800/200; 800/235; 800/250; 800/DIG. 56; 435/412; 435/424; 435/430; 435/430.1; 47/58; 47/DIG. 1
[58] Field of Search ........................ 800/200, 235, 800/250, DIG. 56; 435/412, 424, 430; 47/58, DIG. 1

[56] References Cited

U.S. PATENT DOCUMENTS 5,276,265  1/1994  Fullerton .............................. 800/200

OTHER PUBLICATIONS

Hallauer et al., In Corn and Corn Improvement. Third Edition. Sprague et al., eds. ASA–CSSA–SSSA. Ch. 8:463–564, Jan. 1988.

*Primary Examiner*—Gary Benzion
*Assistant Examiner*—Thanda Wai
*Attorney, Agent, or Firm*—Thomas Hoxie

[57] ABSTRACT

According to the invention, there is provided an inbred corn line, designated CG00766. This invention thus relates to the plants and seeds of inbred corn line CG00766 and to methods for producing a corn plant produced by crossing the inbred line CG00766 with itself or with another corn line. This invention further relates to hybrid corn seeds and plants produced by crossing the inbred line CG00766 with another corn line.

16 Claims, No Drawings

INBRED CORN LINE CG00766

This application is a continuation of Ser. No. 08/391,906, filed Feb. 21, 1995, now abandoned.

FIELD OF THE INVENTION

This invention is in the field of hybrid corn (*Zea mays* L.) plant breeding, specifically relating to an inbred corn line designated CG00766.

BACKGROUND OF THE INVENTION

Of all the crops produced by U.S. farmers, corn is the crop that has the most economic value. Corn is utilized as livestock feed, as a basis for human consumption, as raw material for industry and as raw material for the production of ethanol. The primary use of farmer produced field corn is for livestock feed. This includes feed for hogs, beef cattle, dairy cows and poultry.

Human consumption of corn includes direct consumption of sweet corn and as snacks after extruder cooking, ground corn eaten as grits, corn meal and corn flour. Corn oil is also used as a high grade cooking oil, salad oil and in margarine. Corn is used in the production of some starches and syrups. Another important use is in the production of sweeteners used in soft drinks.

The wet-milling and dry-milling processes also produce corn starch and corn flour that have applications in industry. Some of these uses include building materials, the paper industry, textiles and starches.

The seed of inbred corn line CG00766, the plant produced by the inbred seed, hybrid seed produced from the crossing of the inbred, the hybrid corn plant grown from said seed, and various parts of the inbred and hybrid corn plant can be utilized for human food, livestock feed, and as a raw material in industry.

One of the major reasons for the economic importance of corn and the large acreages planted to the crop are the hybridization of the corn plant and the continued improvement, by researchers, of the genetic stock that is used to produce the seed grown by farmers. This process has been on-going since its beginning in the early part of the century. The average bushel per acre yield for the American farmer has gone from around 30 in the middle of the 1930's (before hybrids became dominant) to the present average of close to 120. While not all of this four-fold increase can be attributed to genetic improvement (availability of relatively cheap nitrogen and improvements in farming practices are two other components), a good share of it can.

The physical structure of the corn plant provides the corn breeder with opportunities either to cross a plant with another plant or to self-pollinate a given plant. Since the male inflorescence (the tassel) and the female inflorescence (the ear) are physically separated from each other on the plant, the breeder has the ability to mate plants as desired with ease. Similar physical manipulations are used both for cross-pollinating and for self-pollinating a corn plant. The silks (stigmae of corn female florets) are protected from pollination until pollen is collected from the male inflorescence. For cross-pollination, pollen from one plant is distributed on the silks of another plant, while for self-pollination, pollen from a plant is distributed on silks of the same plant. Sib-pollination is a type of cross-pollination in which both plants are closely related genetically. Cross-pollination and self-pollination techniques are used in the development of corn hybrids. Self-pollination and sib-pollination increase the level of inbreeding in progeny plants, leading to fixation of alleles. With continued inbreeding comes a larger reduction in vigor and productivity. This phenomenon is known as inbreeding depression. The progeny from the crossing of two inbred lines is a first generation ($F_1$) hybrid, which has better productivity and agronomic characteristics than either of the inbred parents. This phenomenon is called hybrid vigor or heterosis. Heterosis is reduced markedly in succeeding generations ($F_2$, $F_3$, etc.) making it economically justifiable for the farmer to obtain $F_1$ seed each year. As a result, the hybrid corn seed industry benefits both farmers and producers of hybrid corn seed.

Corn is a highly variable species. For hundreds of years, corn breeding consisted of isolation and selection of open-pollinated varieties. Native Americans evolved many different varieties since the domestication of corn in prehistory. During the course of the nineteenth century, North American farmers and seedsmen developed a wide array of open-pollinated varieties, many of which resulted from an intentional or an accidental cross between two very different types of corn: the Southern Dents, which resemble varieties still grown in Mexico, and the Northern Flints, which seem to have moved from the Guatemalan highlands into the northerly parts of the United States and into Canada. The open-pollinated varieties which were developed during this time were maintained by selection of desirable ears from within the variety for use as foundation seed stock. The only pollination control which was practiced to generate the seed was isolation of the seed crop from pollen from other varieties. Experimentation with inbreeding in open-pollinated varieties showed that it invariably led to a marked reduction in plant vigor and stature, as well as in productivity.

In the early twentieth century, researchers discovered that vigor was restored when a line inbred from an open-pollinated variety was crossed to another, usually unrelated, inbred, and that the resulting hybrids were not only more uniform than open-pollinated varieties, but in many cases were more productive as well. Many of the inbreds developed from open-pollinated varieties were remarkably unproductive, however, which made $F_1$ seed quite expensive to produce in any volume. By the 1930's seedsmen were offering four-way or double crosses to growers. These consisted of a cross between two single crosses, which in turn were each crosses between two inbred lines. In this way, only a small quantity of single cross seed was required, and the seed sold to growers was produced on $F_1$ hybrids. Four-way crosses dominated the seed industry until the late 1950's, when three-way crosses were offered to growers. Three way crosses consist of seed produced on a single cross hybrid with an inbred line as the pollinator. Through the efforts of public and private corn breeders, inbred lines were selected to be more productive and vigorous than the earlier selections from the open-pollinated varieties, and by the early 1970's, single cross seed was readily available to growers. Presently, the overwhelming majority of hybrid corn seed sold in the United States is single cross seed.

The method of hybridization in corn first involves the development of inbred lines. Inbred lines are commonly developed through some variation of pedigree breeding, wherein the plant breeder maintains the identity of each new line throughout the inbreeding process. To initiate the pedigree breeding process, the breeder may make an $F_1$ cross between two existing inbred lines which complement each other for traits for which improvement is desired, and which cross well with other inbreds from other genetic backgrounds to make commercial hybrids. The $F_1$ is selfed to provide $F_2$ seed, which is planted and selfed to produce the $S_2$ or $F_3$ generation. $S_2$ lines are planted ear-to-row, and self-pollinations are made within individual rows. Rows which do not provide a desirable phenotype are discarded. Selected ears are planted ear-to-row, and this process repeats until substantial homozygosity is attainted, usually by the $S_6$ or $S_7$ generation. Once homozygosity is attained, the inbred can be maintained in open-pollinated isolations.

Corn breeders in general structure their efforts to take advantage of known heterotic patterns; that is, they use their knowledge of which inbreds make good hybrids with which other inbreds, and they ensure that genetic material from these hererotic pools does not cross over into opposing pools. A highly successful heterotic pattern in the United States corn belt has been to use lines from a population known as Iowa Stiff Stalk Synthetic crossed with lines having more or less of a Lancaster background to provide hybrids for growers. Lancaster was a relatively unimportant open-pollinated variety, until it was discovered in the early years of inbred/hybrid development that it provided an outstanding source of lines with good general combining ability. Other heterotic patterns have also been developed, primarily for the northern and southern regions of the United States. Breeders have understandably been reluctant to use competitive private company hybrids as source material, because, in such instances, it will usually not be known where derived lines fit in a heterotic pattern (Hallauer et at., "Corn Breeding", Corn and Corn Improvement pp. 463–564, (1988)). As well, using competitors' hybrids as source germplasm risks the dispersal of existing hererotic patterns; many breeders feel that introducing, for example, Lancaster material into an Iowa Stiff Stalk background would lessen their ability to develop lines which could be crossed to Lancaster-derived inbreds. Unless it is known that a competitor's hybrid was genetically distinct from a breeder's own material, it is considered to be a more risky approach to improvement of a hererotic pool than utilizing known material. When the source population of CG00766 was developed, it was not clear that a successful, usable commercial line would have been the result, since it was not known at the time where such an inbred could fit into any heterotic pattern.

Even restricting efforts to known heterotic patterns, a breeder can never be certain that a given cross will provide an improved inbred. The nature of heterosis is not at all well understoood. No one knows why, for example, B73×Mo17 was such an advance in productivity over previous hybrids. To say they are heterotic is uninformative: it merely describes what has been observed without explaining the phenomenon. Part of the uncertainty results from the mode of inheritance of many traits of interest, and the mathematics of genetically segregating populations. For example, the trait of chief interest in corn, productivity of marketable grain, is not simply inherited, but instead derives from the action of many genes of relatively small effect. This type of inheritance, known as quantitative inheritance, has been extensively studied from a theoretical standpoint, and certain aspects of the behaviour of segregating populations can be mathematically predicted. One finding is that the probability of obtaining a specific homozygous inbred decreases exponentially with the number of segregating loci for a given trait. Allard (*Principles of Plant Breeding* (1960), p. 68) teaches that, from a population segregating at n loci, with each locus having only two variants of equal frequency (which is the case in a population derived from an $F_1$ between two inbred lines), $2^n$ homozygous genotypes are possible, two of which are the parental genotypes. Thus, if a source population was segregating at only twenty loci, the probability of obtaining any given inbred genotype from this population is less than one in a million. The probability decreases very quickly with more heterozygous loci. Also, if there are loci with more than two variants, the number of possible homozygotes increases and the probability of retrieving a given inbred genotype decreases. The number of loci which affect the trait of gross productivity has been variously estimated at 10 to 1000. In addition, a breeder must pay attention to agronomic traits such as maturity, stalk quality, root quality, grain quality, resistance to diseases and insects, and many others, some of which appear to be negatively correlated with productivity. The total number of genetic loci in the corn genome has been conservatively estimated to be greater than $10^5$.

The objective of a plant breeder when developing a new inbred line of corn is to combine the highest number of desirable alleles into a single isolate as possible. No parent line contains all desirable alleles at all loci, and the breeder hopes to introgress a higher frequency of favorable alleles into resulting progenies. However, with the current state of the art, a breeder is generally not able to define which allele at any given locus is desirable, and for most traits of interest, he does not have information about which genetic loci are involved in influencing the trait. His primary tool to measure the genotypes of progenies is phenotypic evaluation. The phenotype of a plant is influenced both by its genotype and the environment in which it is grown, so the phenotypic measure of a plant is only an indirect measure of its genotype. When environmental effects are large relative to the genotypic effects, it is said that the trait has low heritability. The breeder must evaluate traits of low heritability in many different environments in order to be reasonably sure that he has an accurate estimate of the genotypic effect. Productivity of marketable grain is such a trait, according to years of breeding experience and numerous scientific publications.

The requirement of evaluating genotypes in different environments places serious restraints on the corn breeder in terms of the number of genotypes he will be able to evaluate. The large number of possible genotypes, coupled with the small sample size from a segregating population, make it unpredictable that a breeder will be able to invent a new corn inbred which is a measurable improvement over its parents.

The invention of new inbred lines and of new hybrids is extremely important to the companies in the hybrid seed corn industry that have investments in research. Much effort is given to the research and development of these inbreds and hybrids. The breeding and selection of inbred lines is a highly specialized skill. It involves many years of inbreeding, skilled selection, correct statistical testing, and decision making.

Techniques involving the tissue culture of corn cells and plant parts have been developed to the point that it is now possible to regenerate plants from nearly all genotypes, by varying the culture media in which the cells or parts are cultured. Based upon experience with other inbreds with somewhat similar genetic background, it is anticipated that inbred corn line CG00766 will readily provide regenerable cells in culture of cells or plant pans.

SUMMARY OF THE INVENTION

According to the invention, there is provided a novel inbred corn line, designated CG00766. This invention thus relates to the seeds of inbred corn line CG00766, to the plants of inbred corn line CG00766 and to methods for producing a corn plant produced by crossing the inbred line CG00766 with itself or another corn line. This invention further relates to hybrid corn seeds and plants produced by crossing the inbred line CG00766 with another corn line.

DEFINITIONS

This section will outline the definitions of terms used herein.

The following traits are evaluated in Tables 4a through 4h:

Yield (Bushels/Acre).

Yield in bushels/acre is the actual yield of the grain at harvest adjusted to 15.5% moisture.

Percent Moisture.

The percent moisture is the water content by weight of the grain at harvest.

Percent Erect.

The percent erect, a measure of standability, is the percentage of plant stalks that are not broken below the ear at harvest.

Harvest Roots.

Harvest roots is a visual rating. It is based on the number of plants that are root-lodged (leaning from the vertical at an approximate 30° angle or greater) at the time of harvest. The ratings range from 1 to 9. A rating of 1 equals no plants root-lodged and a rating of 9 equals all plants root-lodged.

Percent Dropped Ears.

The percent dropped ears is the percentage of plants whose ears have fallen to the ground at the time of harvest.

Percent Barren Plants.

The percent barren plants is the percentage of plants that produced no ears.

Intactness.

Intactness is a visual rating based on the percentage of leaf and stalk matter remaining above the top ear at harvest. The ratings range from 1 to 9. A rating of 1 equals all matter remaining (intact) and a rating of 9 equals all matter gone or the stalk broken over just above the ear.

Percent Green.

The percent green is the percentage of the total ear, leaf and stalk matter still green at the time of data collection, approximately physiological maturity.

Value.

Value is a simple index which takes into account market price for grain corn and the cost of drying to storage moisture (15.5%). It is expressed in dollars per acre.

The following traits described in Table 1 (following) are rated on a scale of 1 to 9, in reference to check inbred varieties:

Leaf attitude describes the manner in which leaves of an inbred variety of corn are arrayed on the plant. A rating of 1 indicates the plant has very upright leaves, 9 is drooping leaves.

Mid-pollen date and mid-silking date rate the flowering time relative to appropriate check inbred lines of corn. A rating of 1 indicates very early flowering, and 9 indicates very late to flower.

Anthocyanin pigmentation in various plant parts (glumes, glume bands, anthers, silks, leaf sheaths, internodes, brace roots) provides a visual rating of the intensity of red or purple coloration in these plant parts. A rating of 1 indicates no anthocyanin pigmentation, and 9 indicates heavy pigmentation.

Tassel branch shape describes how the tassel branches are arrayed in the male inflorescence. A rating of 1 indicates very upright tassel branches, and 9 indicates drooping tassel branches.

Number of primary tassel branches is self-explanatory. A rating of 1 indicates 1 to 3 branches, and 9 indicates more than 20 branches.

The length of the tassel main axis both above the uppermost side branch and above the lowermost side branch is self-explanatory. A rating of 1 indicates very short, and 9 indicates very long tassel main axis.

Plant height is self-explanatory. A rating of 1 indicates short, and 9 is tall.

Height of ear insertion is self-explanatory. A rating of 1 indicates low height of insertion, and 9 is high.

Leaf blade width is self-explanatory. A rating of 1 indicates narrow, and 9 indicates wide leaves.

Shank length and husk length are self-explanatory. A rating of 1 indicates short, and 9 indicates long shanks or husks.

Ear shape describes the amount of taper found in the ears, with a rating of 1 indicating no taper (cylindrical shape of the ears), and 9 indicates much taper (conical ears).

Number of kernel rows is self-explanatory. A rating of 1 indicates fewer than 8 kernel rows, and 9 indicates greater than 22 kernel rows.

Grain type rates the flintiness of the grain. A rating of 1 indicates a fully flint kernel type, and 9 indicates a floury kernel.

Grain tip color and grain flank color are self-explanatory. A rating of 1 indicates white, and 9 indicates red pigmentation.

Cob diameter, ear diameter, and ear length are self-explanatory. A rating of 1 indicates small diameter or short length, and 9 indicates larger diameter or long length.

Cob color is self-explanatory. A rating of 1 indicates white cob, and 9 indicates red cob.

TABLE 1

Description of CG00766 compared to MBS847

| Plant characteristic | CG00766 | MBS847 | Description of CG00766 |
|---|---|---|---|
| Leaf attitude | 3 | 3 | half upright |
| Mid-pollen date* | 8 | 5 | late |
| Mid-silking date* | 8 | 5 | late |
| Anthocyanin in glumes | 3 | 3 | weak |
| Anthocyanin in glume band | 1 | 1 | absent |
| Anthocyanin in anthers | 5 | 3 | medium |
| Anthocyanin in silks | 2 | 2 | very weak |
| Anthocyanin in leaf sheath | 1 | 1 | absent |
| Compactness of tassel axis | 5 | 5 | medium |
| Tassel branch shape | 3 | 3–5 | half upright |
| Number of primary tassel branches | 1 | 5 | 1 to 3 |
| Length of tassel branch main axis above the uppermost side branch | 6 | 5 | medium |
| Length of tassel branch main axis above the lowest side branch | 4 | 5 | medium |
| Anthocyanin of inter-nodes | 1 | 1 | absent |
| Anthocyanin of brace roots | 7 | 3 | strong |
| Plant height** | 5 | 5 | medium |
| Height of ear insertion | 2 | 5 | low |
| Leaf blade width | 5 | 5 | medium |
| Shank length | 3 | 7 | short |

TABLE 1-continued

Description of CG00766 compared to MBS847

| Plant characteristic | CG00766 | MBS847 | Description of CG00766 |
|---|---|---|---|
| Husk lentgh | 7 | 5 | long |
| Ear Shape | 2 | 2 | cylindro-conical |
| Number of kernel rows | 4 | 5 | 12 to 14 |
| Grain type | 4 | 5 | flint/dent to dent |
| Grain tip color | 3 | 4–5 | yelllow |
| Grain flank color | 5 | 5 | orange |
| Cob diameter | 4 | 5 | medium |
| Ear diameter | 4 | 5 | medium |
| Ear length | 6 | 5 | medium |
| Cob color | 9 | 9 | red |

*Mid-pollen date standards Standards are Mo17 with a score of 7 and B73 with a score of 9
*Mid-silk date standards Standards are Mo17 with a score of 7 and B73 with a score of 9
**Plant height standards Standards for a score of 7 are Mo17 and A632
Standard for a score of 5 is W182E
Standard for a score of 3 is W117

The following traits are evaluated in Table 2a (following):

Plant height is serf-explanatory.

Ear height is self-explanatory.

Initial pollen is stated as number of days from planting to the first pollen shed observed in the variety.

Initial silk is stated as number of days from planting to the first silks observed in the variety.

Mid silk is stated as number of days and as heat units from planting to the full silking observed in the variety. Heat units are calculated as below.

Final pollen is stated as number of days from planting to the last pollen shed observed in the variety.

Mid pollen is stated both as number of days and as heat units from planting to the date of full pollen shed observed in the variety. Heat units are calculated on a daily basis as ((Maximum temperature in degrees Fahrenheit—Minimum temperature in degrees Fahrenheit)/2)—50, with the constraint that temperatures above 86° F. are counted as 86° F., and temperatures below 50° F. are counted as 50° F.

Final silk is stated as number of days from planting to the last silks observed to emerge in the variety.

Number of tassel branches is self-explanatory.

Tassel size rating describes the size of the tassel, in which a rating of 1 indicates a small tassel and 9 indicates a large tassel.

Kernels per kilogram is self-explanatory. The data is collected and calculated at 15.5% moisture.

Percent of large kernels is the percentage of kernels which pass through a $^{24}/_{64}$ inch round sizing screen but not through a $^{21}/_{64}$ inch round sizing screen.

Percent of medium kernels is the percentage of kernels which pass through a $^{21}/_{64}$ inch round sizing screen but not through an $^{18}/_{64}$ inch round sizing screen.

Percent of small kernels is the percentage of kernels which pass through a $^{18}/_{64}$ inch round sizing screen but not through a $^{33}/_{128}$ inch round sizing screen.

Percent of round kernels is the percentage of kernels which do not pass through a $^{13}/_{64}$ inch slot sizing screen.

Percent of discard kernels is the percentage of kernels which pass through a $^{33}/_{128}$ inch round sizing screen plus the percentage of kernels which do not pass through a $^{26}/_{64}$ inch round sizing screen.

Number of 80000 is the number of 80,000-kernel units produced per hectare, accounting for yield and seed sizes, after discard seed has been excluded.

TABLE 2a

Agronomic comparisons of CG00766 with FR1064 and LH132.

| Trait | CG00766 | FR1064 | LH132 | # |
|---|---|---|---|---|
| Plant height (cm) | 178 | 176 | 172 | 3 |
| Ear height (cm) | 82 | 98 | 69 | 3 |
| Initial pollen (days) | 73.9 | 75.4 | 75.2 | 6 |
| Initial silk (days) | 74.0 | 75.1 | 75.1 | 6 |
| Mid pollen (days) | 75.2 | 77.1 | 76.7 | 6 |
| Mid silk (days) | 75.8 | 77.4 | 77.3 | 6 |
| Final pollen (days) | 82.5 | 85.0 | 83.0 | 2 |
| Final silk (days) | 81.5 | 85.0 | 84.0 | 2 |
| Mid pollen (heat units) | 1464 | 1504 | 1496 | 6 |
| Mid silk (heat units) | 1473 | 1509 | 1506 | 6 |
| Number of tassel branches | 2.5 | 7.0 | 8.5 | 2 |
| Tassel size rating (1 = large, 9 = small) | 7.9 | 5.4 | 5.7 | 3 |
| Kernels per kilogram | 3541 | 3817 | 3504 | 3 |
| Percent of large kernels | 35.7 | 15.3 | 8.4 | 5 |
| Percent of medium kernels | 47.4 | 47.5 | 44.6 | 5 |
| Percent of small kernels | 16.4 | 37.0 | 47.3 | 5 |
| Percent of round kernels | 69.1 | 22.0 | 21.8 | 5 |
| Percent of discard kernels | 2.8 | 9.7 | 7.8 | 3 |
| Number of 80000 kernel units per hectare | 154.2 | 171.3 | 151.4 | 6 |

The following disease resistance traits are evaluated in Table 2b:

Disease (causative organism):
  Northern corn leaf blight Race 1 (*Exserohilum turcicum*)
  Southern corn leaf blight (*Bipolaris maydis*)
  Gray leaf spot (*Cercospora zeae-maydis*)
  Common rust (*Puccinia sorghi*)
  Anthracnose leaf blight (*Colletotrichum graminicola*)
  Eyespot (*Kabatiella zeae*)
  Carbonum leaf spot (*Helminthosporium carbonum*)
  Gibberella ear mold (*Gibberella zeae*)
  Fusarium kernel rot (*Fusarium moniliforme*)
  Diplodia ear rot (*Diplodia zeae*)
  Common smut (*Ustilago maydis*)

These diseases are rated on a 1 to 9 basis, with 1 rating as very resistant, and 9 rating as very susceptible.

TABLE 2b

Disease resistance comparisons of CG00766 with FR1064 and LH132 (ratings: 1 = very resistant, 9 = very susceptible).

| Disease | CG00766 | FR1064 | LH132 |
|---|---|---|---|
| Northern corn leaf | 3.5 | 5.9 | 6.1 |
| Southern corn leaf | 1.8 | 5.8 | 6.1 |
| Gray leaf spot | 4.3 | 4.8 | 7.2 |
| Common rust | 2.7 | 5.5 | 5.3 |
| Anthracnose leaf | 1.0 | 3.0 | 3.1 |
| Eyespot | 3.6 | 4.0 | 4.8 |
| Carbonum leaf spot | 2.0 | 5.0 | 6.1 |
| Gibberella ear mold | 2.5 | 5.0 | 6.5 |
| Fusarium kernel rot | 2.5 | 4.0 | 5.0 |

TABLE 2b-continued

Disease resistance comparisons of CG00766 with FR1064 and LH132 (ratings: 1 = very resistant, 9 = very susceptible).

| Disease | CG00766 | FR1064 | LH132 |
|---|---|---|---|
| Diplodia ear rot | 7.5 | 6.0 | 6.3 |
| Common smut | 1.0 | 1.3 | 1.2 |

DETAILED DESCRIPTION OF THE INVENTION

Inbred corn line CG00766 is a yellow dent corn with superior characteristics and provides a good parental line in crosses for producing first generation ($F_1$) hybrid corn.

Inbred corn line CG00766 was selected for uniformity and agronomic traits using standard pedigree ear-row selection at Marion, Iowa and Kaunakakai, Hawaii. The source population of CG00766 was a cross between two partially inbred isolates from the $F_2$generation of the commercial single cross Pioneer 3540. The inbred was evaluated as a line and in numerous crosses by the Marion Research Station and other research stations across the central and northern corn belt. Thus the line was evaluated for general and specific combining ability.

Inbred corn line CG00766 is adapted to the central and northern corn belt and can be used advantageously in producing hybrids that are from approximately 90 day relative maturity to 110 day relative maturity based on the Minnesota Relative Maturity Rating System for harvest moisture of the grain. The inbred is a medium height inbred with pale leaves and some chlorortic flecks. It sheds pollen best under moderate temperatures. It sheds less than an average quantity of pollen. This line produces medium height hybrids with good ear flex and excellent grain quality.

Inbred corn line CG00766 has shown uniformity and stability for all traits as described in the following variety description information. It has been self-pollinated and ear-rowed a sufficient number of generations with careful attention paid to uniformity of plant type to insure relative homozygosity and phenotypic stability. The line has been increased by hand and in isolated fields with continued observations for uniformity. No particular variant traits have been observed or are expected in CG00766.

The inbred CG00766 is a proprietary inbred of Ciba Seeds.

Inbred corn line CG00766 can be compared to the publicly available inbred MBS847. MBS847 and CG00766 are of somewhat similar genetic background and would be used to make hybrids of similar maturity. The characteristics of CG00766 versus MBS847 are summarized below in Table 1.

Inbred corn line CG00766 can be compared to the popular publicly available inbreds FR1064 and LH132. While CG00766 is of different background from these two lines, it will be used quite similarly to FR1064 and LH132 in hybrid combinations. Comparisons of CG00766 with FR1064 and LH132 are presented in Tables 2a and 2b.

Restriction fragment length polymorphisms for CG00766 and several disclosed inbreds of similar genetic background are shown in Table 3 below.

TABLE 3

Restriction fragment length polymorphisms for CG00766 and check inbreds of similar genetic background.

| RFLP locus | CG00766 | PHK29 | PHK35 | PHM10 | PHN82 | PHP55 |
|---|---|---|---|---|---|---|
| B05.09 | DD | DD | DD | DD | DD | DD |
| B05.47 | EE | EE | EE | EE | EE | EE |
| B05.71 | CC | CC | AA | BB | BB | BB |
| B06.32 | AA | DD | AA | BB | BB | BB |
| B07.71 | BB | BB | BB | BB | CC | CC |
| B08.15 | CC | CC | CC | CC | CC | CC |
| B16.06 | CC | CC | CC | CC | BB | CC |
| N107 | CC | CC | CC | CC | AA | AA |
| N110 | CC | CC | CC | CC | CC | CC |
| N114 | AB | BB | AA | BB | CC | CC |
| N237 | DD | CC | DD | BB | BB | BB |
| N239 | BB | AA | BB | AA | AA | AA |
| N256 | BB | BB | CC | CC | BB | CC |
| N260 | DD | BB | BB | BB | DD | DD |
| N262 | CC | CC | EE | FF | AA | AA |
| N274 | BB | AA | AA | BB | CC | BB |
| N285 | CC | — | CC | CC | BB | AA |
| N291 | AA | AA | AA | AA | AA | AA |
| N295 | DD | DD | DD | CC | AA | AA |
| N373 | BB | AA | BB | CC | AA | CC |
| N432 | BB | BB | BB | BB | DD | BB |
| N560 | DD | DD | DD | DD | AA | DD |
| U28 | CC | CC | CC | CC | CC | CC |
| U31 | GG | EE | EE | GG | GG | GG |
| U32 | CC | AA | AA | AA | CC | CC |
| U48 | II | II | II | EE | II | II |
| U51 | CC | AA | CC | CC | CC | CC |
| U57 | CC | BB | BB | BB | CC | CC |
| U58 | BB | BB | DD | DD | CC | CC |
| U157 | AA | AA | AA | EE | EE | EE |
| U89 | BB | AA | AA | BB | BB | BB |
| U90 | BC | BB | BB | CC | CC | BB |
| U95 | CC | CC | CC | AA | AA | AA |
| U109 | CC | DD | CC | AA | BB | BB |
| U121 | AA | BB | BB | AA | CC | CC |
| U130 | CC | AA | AB | CC | CC | CC |
| U136 | CC | BB | CC | CC | CC | CC |
| U166 | CC | CC | CC | CC | CC | CC |
| # different from CG00766 | | 18/38 | 14/37 | 18/38 | 21/38 | 18/38 |

In terms of genetic background, CG00766 is closest to PHM10 (U.S. Pat. No. 5,097,095 and PVP Certificate No. 8900312), which was derived from a cross between G39 (PVP Certificate 8300115) and 207 (PVP Certificate No. 8300144). Pioneer 3540 was very similar genetically to this cross, according to proprietary RFLTP information. PHN82 (U.S. Pat. No. 5,157,206 and PVP Certificate No. 8900317) and PHP55 (U.S. Pat. No. 5,159,134 and PVP Certificate No. 8900318) were derived fro a 207 background. PHK29 (U.S. Pat. No. 4,812,600 and PVP Certificate No. 8700214) and PHK35 (U.S. Pat. No. 5,095,174 and PVP Certificate No. 8900311) were derived from an Iowa Stiff Stalk Synthetic background, as does G39, according to proprietary RFLP information.

This invention is also directed to methods for producing a corn plant by crossing a first parent corn plant with a second parent corn plant wherein the first or second corn plant is the inbred corn plant from the line CG00766. Further both first and second parent corn plants may be from the inbred line CG00766. Thus, any methods using the inbred corn line CG00766 are part of the invention: backcrosses, hybrid breeding, and crosses to populations. Any plants produced using inbred corn line CG00766 as a parent are within the scope of this invention. A preferred use of inbred corn line CG00766 is for the production of inbred seed of CG00766, by crossing CG00766 with another plant of CG00766, or by directly self-pollinating a plant of CG00766. An especially preferred use of the inbred corn line CG00766 is for the production of first generation ($F_1$) corn hybrid seeds which produce plants with superior characteristics, by crossing CG00766 either as a seed line or as a pollen line to another, distinct inbred line, both for sale to growers to produce market gain, and for inbreeding and development of improved inbred lines by its proprietors.

As used herein, the term "plant" includes plant cells, plant protoplasts, plant cell of tissue culture from which corn plants can be regenerated, plant calli, plant clumps, and plant cells that are intact in plants or parts of plants such as pollen, flowers, kernels, ears, cobs, leaves, husks, stalks, and the like.

Duncan, Williams, Zehr, and Widholm, *Planta*, (1985) 165, 322–332, reflects that 97% of the plants cultured which produced callus were capable of plant regeneration. Subsequent experiments with both inbreds and hybrids produced 91% regenerable callus which produced plants. In a further study in 1988, Songstad, Duncan and Widholm in *Plant Cell Reports* (1988), 7,262–265 reports several media additions which enhance regenerability of callus of two inbred lines. Other published reports also indicated that "nontraditional" tissues are capable of producing somatic embryogenesis and plant regeneration. K. P. Rao, et al., *Maize Genetics Cooperation Newsletter*, 60, 64–65 (1986) refers to some embryogenesis from glume callus cultures and B. V. Conger, et al., *Plant Cell Reports*, 6, 345–347 (1987) indicates somatic embryogenesis from the tissue cultures of corn leaf segments. Thus, it is clear from the literature that the state of the art is such that these methods of obtaining plants are, and were, conventional in the sense that they are routinely used and have a very high rate of success.

Tissue culture of corn is described in EP-A-0 160 390, incorporated herein by reference. Corn tissue culture procedures are also described in Green and Rhodes, "Plant Regeneration in Tissue Culture of Maize," *Maize for Biological Research* (Plant Molecular Biology Association, Charlottsville, Va. 1982, p. 367–372) and in Duncan, et al., "The Production of Callus Capable of Plant Regeneration from Immature Embryos of Numerous *Zea Mays* Genotypes, 165 *Planta* 322–332 (1985). Thus, another aspect of this invention is to provide cells which upon growth and differentiation produce corn plants having all the physiological and morphological characteristics of inbred corn plant CG00766.

The seed of inbred corn line CG00766, the plant produced from the inbred seed, the hybrid corn plant produced from the crossing of the inbred, hybrid seed, and various parts of the hybrid corn plant can be utilized for human food, livestock feed, and as a raw material in industry.

The results in Table 4a–4h (following) compare CG00766 hybrids to other Ciba Seeds hybrids, both commercial and experimental. In each comparison, the hybrids have an inbred in common which is not CG00766. Each comparison shows the effect of substituting CG00766 for a different inbred; in this way, an idea of general combining ability of CG00766 relative to a range of other inbreds is obtained. The data were averaged across locations and replications and include experiments grown by Ciba Seeds maize research programs in 1991, 1992, 1993 and 1994.

TABLE 4a

Comparison of CG00766 hybrid 4274X with commercial hybrid 4494.

| Hybrid | Yield | % Moist | % Erect | % Push | Harv Roots | Drop Ears | % Barren | Intact | % Green | Final Popn | Value |
|---|---|---|---|---|---|---|---|---|---|---|---|
| 4494 | 168.8 | 20.2 | 96.0 | 66.3 | 1.8 | 0.32 | . | 4.1 | 30.9 | 24.65 | 389.70 |
| 4274X | 159.1 | 18.0 | 97.3 | 80.9 | 1.3 | 0.21 | . | 3.5 | 35.7 | 24.65 | 377.54 |
| D | 9.7 | 2.2 | −1.3 | −14.6 | 0.5 | 0.10 | . | 0.7 | −4.7 | 0.00 | 12.17 |
| LSD 0.01 | 7.9 | 0.6 | 1.2 | 9.6 | 0.7 | 0.44 | . | 0.7 | 6.2 | 0.43 | 18.06 |
| LSD 0.05 | 6.0 | 0.4 | 0.9 | 7.3 | 0.5 | 0.33 | . | 0.5 | 4.5 | 0.32 | 13.74 |
| LSD 0.10 | 5.0 | 0.4 | 0.8 | 6.1 | 0.4 | 0.27 | . | 0.4 | 3.8 | 0.27 | 11.53 |
| LOCATIONS | 49 | 49 | 37 | 40 | 15 | 27 | 0 | 46 | 24 | 51 | 49 |
|  | — | +++ | +++ | +++ | ++ | 0 | X | +++ | — | X | — |

TABLE 4b

Comparison of CG00766 hybrid 2138X with commercial hybrid 4372.

| Hybrid | Yield | % Moist | % Erect | % Push | Harv Roots | Drop Ears | % Barren | Intact | % Green | Final Popn | Value |
|---|---|---|---|---|---|---|---|---|---|---|---|
| 4372 | 158.6 | 20.6 | 98.1 | 50.2 | 1.6 | 0.55 | . | 5.9 | 22.5 | 23.92 | 362.48 |
| 2138X | 156.2 | 17.7 | 98.6 | 56.4 | 1.3 | 0.08 | . | 5.2 | 32.0 | 23.83 | 372.43 |
| D | 2.5 | 3.0 | −0.5 | −6.2 | 0.4 | 0.46 | . | 0.7 | −9.5 | 0.08 | −9.95 |
| LSD 0.01 | 8.9 | 1.1 | 1.7 | 22.4 | 1.3 | 1.11 | . | 0.6 | 9.2 | 0.72 | 22.10 |
| LSD 0.05 | 6.5 | 0.8 | 1.2 | 16.0 | 0.9 | 0.73 | . | 0.4 | 5.9 | 0.53 | 16.04 |
| LSD 0.10 | 5.3 | 0.7 | 1.0 | 13.1 | 0.7 | 0.58 | . | 0.3 | 4.6 | 0.44 | 13.21 |
| LOCATIONS | 17 | 17 | 11 | 14 | 8 | 7 | 0 | 12 | 6 | 18 | 17 |
|  | 0 | +++ | 0 | 0 | 0 | 0 | X | +++ | +++ | X | 0 |

TABLE 4c

Comparison of CG00766 hybrid 4288X with experimental hybrid 4227X.

| Hybrid | Yield | % Moist | % Erect | % Push | Harv Roots | Drop Ears | % Barren | Intact | % Green | Final Popn | Value |
|---|---|---|---|---|---|---|---|---|---|---|---|
| 4227X | 174.0 | 19.2 | 97.1 | 83.9 | 2.5 | 0.46 | 9.40 | 3.4 | 43.1 | 25.04 | 406.18 |
| 4288X | 168.1 | 18.5 | 97.4 | 80.7 | 2.4 | 0.28 | 3.10 | 5.1 | 35.7 | 24.40 | 396.22 |
| D | 5.9 | 0.7 | −0.4 | 3.3 | 0.1 | 0.18 | 6.30 | −2.0 | 7.5 | 0.64 | 9.97 |
| LSD 0.01 | 10.2 | 0.6 | 2.8 | 6.6 | 0.6 | 0.70 | . | 0.8 | 7.3 | 0.74 | 24.34 |
| LSD 0.05 | 7.7 | 0.5 | 2.1 | 4.9 | 0.4 | 0.49 | . | 0.6 | 5.4 | 0.56 | 18.52 |
| LSD 0.10 | 6.5 | 0.4 | 1.7 | 4.1 | 0.4 | 0.40 | . | 0.5 | 4.5 | 0.47 | 15.54 |
| LOCATIONS | 42 | 42 | 20 | 29 | 13 | 12 | 1 | 33 | 23 | 44 | 42 |
|  | 0 | +++ | 0 | 0 | 0 | 0 | X | — | — | X | 0 |

TABLE 4d

Comparison of CG00766 hybrid 3192X with experimental hybrid 3200X.

| Hybrid | Yield | % Moist | % Erect | % Push | Harv Roots | Drop Ears | % Barren | Intact | % Green | Final Popn | Value |
|---|---|---|---|---|---|---|---|---|---|---|---|
| 3200X | 167.1 | 20.2 | 95.4 | 35.0 | 1.7 | 0.11 | . | 6.1 | 28.5 | 25.24 | 383.55 |
| 3192X | 163.6 | 19.5 | 98.5 | 68.2 | 1.0 | 0.08 | . | 4.5 | 45.3 | 24.60 | 379.51 |
| D | 3.4 | 0.7 | −3.0 | −33.2 | 0.6 | 0.03 | . | 1.6 | −16.7 | 0.64 | 4.04 |
| LSD 0.01 | 8.6 | 0.6 | 2.8 | 15.3 | 0.8 | 0.23 | . | 0.9 | 13.0 | 0.61 | 20.33 |
| LSD 0.05 | 6.4 | 0.4 | 2.0 | 11.3 | 0.5 | 0.17 | . | 0.6 | 9.3 | 0.46 | 15.10 |
| LSD 0.10 | 5.3 | 0.4 | 1.7 | 9.4 | 0.4 | 0.14 | . | 0.5 | 7.6 | 0.38 | 12.56 |
| LOCATIONS | 32 | 32 | 28 | 30 | 13 | 18 | 0 | 32 | 13 | 32 | 32 |
|  | 0 | +++ | +++ | +++ | ++ | 0 | X | +++ | +++ | X | 0 |

TABLE 4e

Comparison of CG00766 hybrid 3169X with experimental hybrid 3153X.

| Hybrid | Yield | % Moist | % Erect | % Push | Harv Roots | Drop Ears | % Barren | Intact | % Green | Final Popn | Value |
|---|---|---|---|---|---|---|---|---|---|---|---|
| 3153X | 153.4 | 21.8 | 96.4 | 67.9 | 2.0 | 0.23 | . | 4.2 | 36.2 | 25.46 | 345.75 |
| 3169X | 153.2 | 19.7 | 97.1 | 77.2 | 1.3 | 0.20 | . | 3.4 | 41.6 | 25.50 | 356.00 |
| D | 0.2 | 2.1 | −1.3 | −9.3 | 0.7 | 0.02 | . | 0.9 | −5.4 | −0.04 | −10.25 |
| LSD 0.01 | 5.7 | 0.4 | 0.8 | 6.4 | 0.4 | 0.26 | . | 0.4 | 11.2 | 0.17 | 13.83 |
| LSD 0.05 | 4.3 | 0.3 | 0.6 | 4.9 | 0.3 | 0.20 | . | 0.3 | 8.2 | 0.13 | 10.53 |
| LSD 0.10 | 3.6 | 0.3 | 0.5 | 4.1 | 0.3 | 0.16 | . | 0.3 | 6.8 | 0.11 | 8.83 |
| LOCATIONS | 69 | 69 | 61 | 58 | 28 | 34 | 0 | 59 | 25 | 69 | 69 |
|  | 0 | +++ | +++ | +++ | +++ | 0 | X | +++ | 0 | X | + |

TABLE 4f

Comparison of CG00766 hybrid 2151X with experimental hybrid 3173X.

| Hybrid | Yield | % Moist | % Erect | % Push | Harv Roots | Drop Ears | % Barren | Intact | % Green | Final Popn | Value |
|---|---|---|---|---|---|---|---|---|---|---|---|
| 3173X | 162.3 | 21.5 | 99.0 | 81.4 | 2.6 | 0.31 | . | 4.0 | 34.2 | 24.65 | 364.82 |
| 2151X | 160.0 | 19.6 | 99.4 | 87.5 | 1.5 | 0.23 | . | 2.7 | 46.4 | 24.81 | 369.52 |
| D | 2.4 | 1.8 | −0.5 | −6.1 | 1.1 | 0.07 | . | 1.3 | −12.2 | −0.16 | −4.69 |
| LSD 0.01 | 10.9 | 0.7 | 0.7 | 6.6 | 2.3 | 0.63 | . | 0.6 | 23.7 | 0.85 | 25.84 |
| LSD 0.05 | 8.0 | 0.5 | 0.5 | 4.8 | 1.6 | 0.44 | . | 0.4 | 16.3 | 0.63 | 18.95 |
| LSD 0.10 | 6.6 | 0.4 | 0.4 | 4.0 | 1.3 | 0.35 | . | 0.4 | 13.1 | 0.52 | 15.67 |
| LOCATIONS | 21 | 21 | 18 | 18 | 9 | 10 | 0 | 20 | 9 | 24 | 21 |
|  | 0 | +++ | ++ | ++ | 0 | 0 | X | +++ | 0 | X | 0 |

TABLE 4g

Comparison of CG00766 hybrid 2151X with experimental hybrid 2152X.

| Hybrid | Yield | % Moist | % Erect | % Push | Harv Roots | Drop Ears | % Barren | Intact | % Green | Final Popn | Value |
|---|---|---|---|---|---|---|---|---|---|---|---|
| 2152X | 159.0 | 22.0 | 97.7 | 77.1 | 3.3 | 0.10 | . | 4.5 | 29.7 | 25.80 | 354.05 |
| 2151X | 160.3 | 20.4 | 99.4 | 87.9 | 1.4 | 0.18 | . | 2.6 | 49.1 | 25.65 | 366.09 |
| D | −1.4 | 1.6 | −1.7 | −10.7 | 1.9 | −0.08 | . | 1.9 | −19.4 | 0.14 | −12.04 |
| LSD 0.01 | 9.1 | 1.2 | 1.9 | 14.7 | 2.8 | 0.76 | . | 0.9 | 24.0 | 0.37 | 22.42 |
| LSD 0.05 | 6.6 | 0.9 | 1.4 | 10.6 | 1.8 | 0.51 | . | 0.7 | 16.2 | 0.27 | 16.27 |
| LSD 0.10 | 5.4 | 0.7 | 1.1 | 8.7 | 1.4 | 0.41 | . | 0.5 | 13.0 | 0.22 | 13.40 |
| LOCATIONS | 17 | 17 | 15 | 14 | 7 | 8 | 0 | 16 | 8 | 21 | 17 |
|  | 0 | +++ | + | ++ | ++ | 0 | X | +++ | ++ | X | 0 |

TABLE 4h

Traits of CG00766 in hybrid combination compared with other commercial inbreds.

| | Check Hybrid | | | | | | |
|---|---|---|---|---|---|---|---|
| | 4494 | 4372 | 4227X | 3200X | 3153X | 3173X | 2152X |
| Yield | — | 0 | 0 | 0 | 0 | 0 | 0 |
| % H$_2$O | +++ | +++ | +++ | +++ | +++ | +++ | +++ |
| Stalk | +++ | 0 | 0 | +++ | +++ | ++ | + |
| Push | +++ | 0 | 0 | +++ | +++ | ++ | ++ |
| Roots | ++ | 0 | 0 | ++ | +++ | 0 | ++ |
| Drop ears | 0 | 0 | 0 | 0 | 0 | 0 | 0 |
| Intactness | +++ | +++ | — | +++ | +++ | +++ | +++ |
| Staygreen | —— | +++ | — | +++ | 0 | 0 | ++ |
| Value | − | 0 | 0 | 0 | + | 0 | 0 |

+++ = significant (0.01) advantage for CG00766 over check inbred in hybrid combination
++ = significant (0.05) advantage for CG00766 over check inbred in hybrid combination
+ = significant (0.10) advantage for CG00766 over check inbred in hybrid combination
0 = no significant difference between CG00766 and check inbred in hybrid combination
− = significant (0.10) advantage for check inbred over CG00766 in hybrid combination
—— = significant (0.05) advantage for check inbred over CG00766 in hybrid combination
——— = significant (0.01) advantage for check inbred over CG00766 in hybrid combination Table 4a compares a CG00766 hybrid, 4274X, with 4494, an important commercial hybrid for Ciba Seeds. The general background of the common inbred is Oh43. The data show that, while the CG00766 hybrid does not yield the same as 4494, it is much drier, has better stalks, roots and intactness. The overall value of the CG00766 hybrid in comparison with 4494 is slightly lower, but because of its earlier maturity, the CG00766 hybrid would be expected to be grown where 4494 could not be grown.

Table 4b compares a CG00766 hybrid, 2138X, with 4372, an important commercial hybrid for Ciba Seeds. The general background of the common inbred is early Mo17. The CG00766 hybrid yields the same as 4372, is much drier, has better intactness and staygreen. The overall value of the CG00766 hybrid in comparison with 4372 is essentially the same, and because of its earlier maturity, the CG00766 hybrid would be expected to be grown where 4372 could not be grown.

Table 4c compares a CG00766 hybrid, 4288X, with 4227X, a Ciba Seeds advanced experimental hybrid. The general background of the common inbred is unclear, since it partially derives from an older commercial hybrid and partially from Mo17. The CG00766 hybrid yields the same as 4227X and is much drier. Agronomic characteristics of the two hybrids do not differ significantly. The overall value of the CG00766 hybrid in comparison with 4227X is essentially the same, and because of its earlier maturity, the CG00766 hybrid would be expected to be grown where 4227X could not be grown.

Table 4d compares a CG00766 hybrid, 3192X, with 3200X, an experimental hybrid from Holden's. The general background of the common inbred is LH82 and LH122. The CG00766 hybrid yields the same as 3200X, is much drier, and has much better agronomics. The overall value of the CG00766 hybrid in comparison with 3200X is essentially the same, and because of its earlier maturity, the CG00766 hybrid would be expected to be grown where 3200X could not be grown.

Table 4e compares a CG00766 hybrid, 3169X, with 3153X, a Ciba Seeds advanced experimental hybrid. The general background of the common inbred is Mo17. The CG00766 hybrid yields the same as 3153X, and is much drier. The stalk, root, and intactness characteristics of the CG00766 hybrid are much better than those of 3153X. The overall value of the CG00766 hybrid in comparison with 3153X is higher, and because of its earlier maturity, the CG00766 hybrid would be expected to be grown where 3153X could not be grown.

Table 4f compares a CG00766 hybrid, 2151X, with 3173X, a Ciba Seeds experimental hybrid. The general background of the common inbred is early Mo17. The CG00766 hybrid yields the same as 3173X, and is much drier, with better stalks and intactness. The overall value of the CG00766 hybrid in comparison with 3173X is essentially the same, and because of its earlier maturity, the CG00766 hybrid would be expected to be grown where 3173X could not be grown.

Table 4g compares a CG00766 hybrid, 2151X, with 2152X, a Ciba Seeds experimental hybrid. The general background of the common inbred is early Mo17. The CG00766 hybrid yields the same as 2152X, and is much drier, along with much improved agronomics. The overall value of the CG00766 hybrid in comparison with 2152X is essentially the same, and because of its earlier maturity, the CG00766 hybrid would be expected to be grown where 2152X could not be grown.

Table 4h briefly summarizes the advantages of substituting CG00766 for other inbreds evaluated in hybrid combination in the foregoing Tables. In general, it can be seen that CG00766 contributes high yield comparable to significantly later hybrids, low harvest moisture, excellent stalks, staygreen and intactness (especially so, given the comparisons with later hybrids, which in the normal course of events are expected to have the better agronomics), and very good root quality.

TABLE 5

Restriction fragment length polymorphism map of Pioneer 3540.

| Locus | Genotype | Locus | Genotype | Locus | Genotype | Locus | Genotype | Locus | Genotype |
|---|---|---|---|---|---|---|---|---|---|
| CG100 | AD | CG561 | CE | CG259 | DG | CG320 | AD | CG317 | AB |
| CG489 | CE | CG267 | CD | CG270 | CC | CG325 | CC | CG334 | AD |
| CG346 | AC | CG354 | BB | CG128 | AD | CG141 | BB | CG454 | DD |
| CG361 | AC | CG341 | BC | CG134 | AC | CG295 | DE | CG337 | BB |
| CG411 | CE | CG125 | DD | CG307 | DD | CG095 | CC | CG080 | EE |
| CG335 | CD | CG041 | CC | CG406 | BE | CG323 | AC | CG123 | AB |
| CG450 | BC | CG279 | CC | CG102 | AD | CG315 | CF | CG437 | BC |
| CG107 | AB | CG265 | CE | CG264 | DD | CG483 | CG | CG492 | BF |
| CG310 | BB | CG303 | CF | CG177 | EE | CG608 | BB | CG302 | BE |
| CG176 | AC | CG329 | AA | CG167 | AB | CG460 | CC | CG122 | DG |
| CG186 | DD | CG573 | AD | CG485 | CC | CG536 | AH | CG168 | AA |

Restriction fragment length polymorphisms were assessed in the source population of CG00766. Of fifty-five RFLP loci characterized, Pioneer 3540 was found to be heterozygous at thirty-four (Table 5, above). Using Allard's formula, this source material is capable of producing 17,179,869,184 distinct homozygous genotypes for the loci characterized, only one of which is CG00766. To put this into perspective, if all possible inbred genotypes (considering only the RFLP loci which have been evaluated) from this source population were to be grown at a commercial density, with each genotype represented by only one plant, nearly 700,000 acres would be filled. It is evident that a person highly trained in the art could start with exactly the same source material, use the same breeding techniques, and develop a new maize inbred, but it would be extremely unlikely to be the same inbred as CG00766. Further, given sampling error and the necessity for testing across numerous environments, a skilled breeder can have no assurance that he will be able to develop a commercially usable inbred line at all from this or any other source population, let alone one which shows the distinct advantages of CG00766.

In a given source population segregating at a number loci, it is reasonable to assume that, in most cases, one parental allele confers an advantage over the other. The magnitude of the advantage will depend upon the locus and the alleles in question. It is the task of the breeder to isolate as many of these favorable alleles into a single progeny as possible. Using the number of segregating RFLP loci as a minimum estimate of segregating loci in the source population of CG00766, it is possible to calculate the number of homozygous genotypes which can be obtained from this source, classifying them according to content of favorable alleles. The results of such calculations are listed in Table 6 (following).

TABLE 6

Distribution of genotypes in a population segregating at 34 loci, according to number of favorable alleles.

| n | Number of possible homozygous genotypes containing n favorable alleies | Probability of obtaining any homozygous genotype containing n favorable alleies | Probability of obtaining a specific homozygous genotype given that the genotype has n favorable alleies | n | Number of possible homozygous genotypes containing n favorable alleies | Probability of obtaining any homozygous genotype containing n favorable alleies | Probability of obtaining a specific homozygous genotype given that the genotype has n favorable alleies |
|---|---|---|---|---|---|---|---|
| 0 | 1 | $6 \times 10^{-11}$ | 1 | 18 | $2.2 \times 10^9$ | $1.3 \times 10^{-1}$ | $4.5 \times 10^{-10}$ |
| 1 | 34 | $2.0 \times 10^{-8}$ | $2.9 \times 10^{-2}$ | 19 | $1.9 \times 10^9$ | $1.1 \times 10^{-1}$ | $5.4 \times 10^{-10}$ |
| 2 | 561 | $3.3 \times 10^{-8}$ | $1.8 \times 10^{-3}$ | 20 | $1.4 \times 10^8$ | $8.1 \times 10^{-2}$ | $7.2 \times 10^{-10}$ |
| 3 | 5890 | $3.5 \times 10^{-7}$ | $1.7 \times 10^{-4}$ | 21 | $9.3 \times 10^8$ | $5.4 \times 10^{-2}$ | $1.1 \times 10^{-9}$ |
| 4 | 4640 | $2.7 \times 10^{-6}$ | $2.2 \times 10^{-5}$ | 22 | $5.5 \times 10^8$ | $3.2 \times 10^{-2}$ | $1.8 \times 10^{-9}$ |
| 5 | $2.8 \times 10^5$ | $1.6 \times 10^{-5}$ | $3.6 \times 10^{-6}$ | 23 | $2.9 \times 10^8$ | $1.7 \times 10^{-2}$ | $3.5 \times 10^{-9}$ |
| 6 | $1.3 \times 10^6$ | $7.8 \times 10^{-5}$ | $7.4 \times 10^{-7}$ | 24 | $1.3 \times 10^8$ | $7.6 \times 10^{-3}$ | $7.6 \times 10^{-9}$ |
| 7 | $5.4 \times 10^6$ | $3.1 \times 10^{-4}$ | $1.9 \times 10^{-7}$ | 25 | $5.3 \times 10^7$ | $3.1 \times 10^{-3}$ | $1.9 \times 10^{-8}$ |
| 8 | $1.8 \times 10^7$ | $1.1 \times 10^{-3}$ | $5.5 \times 10^{-8}$ | 26 | $1.8 \times 10^7$ | $1.1 \times 10^{-3}$ | $5.5 \times 10^{-8}$ |
| 9 | $5.3 \times 10^7$ | $3.1 \times 10^{-3}$ | $1.9 \times 10^{-8}$ | 27 | $5.4 \times 10^6$ | $3.1 \times 10^{-4}$ | $1.9 \times 10^{-7}$ |
| 10 | $1.3 \times 10^8$ | $7.6 \times 10^{-3}$ | $7.6 \times 10^{-8}$ | 28 | $1.3 \times 10^6$ | $7.8 \times 10^{-5}$ | $7.4 \times 10^{-7}$ |
| 11 | $2.9 \times 10^8$ | $1.7 \times 10^{-2}$ | $3.5 \times 10^{-8}$ | 29 | $2.8 \times 10^5$ | $1.6 \times 10^{-5}$ | $3.6 \times 10^{-6}$ |
| 12 | $5.5 \times 10^8$ | $3.2 \times 10^{-2}$ | $1.8 \times 10^{-8}$ | 30 | $4.6 \times 10^4$ | $2.7 \times 10^{-6}$ | $2.2 \times 10^{-5}$ |
| 13 | $9.3 \times 10^8$ | $5.4 \times 10^{-2}$ | $1.1 \times 10^{-8}$ | 31 | 5890 | $3.5 \times 10^{-7}$ | $1.7 \times 10^{-4}$ |
| 14 | $1.4 \times 10^9$ | $8.1 \times 10^{-2}$ | $7.2 \times 10^{-10}$ | 32 | 561 | $3.3 \times 10^{-8}$ | $1.8 \times 10^{-4}$ |
| 15 | $1.9 \times 10^9$ | $1.1 \times 10^{-1}$ | $5.4 \times 10^{-10}$ | 33 | 340 | $2.0 \times 10^{-8}$ | $2.9 \times 10^{-2}$ |
| 16 | $2.2 \times 10^9$ | $1.3 \times 10^{-1}$ | $4.5 \times 10^{-10}$ | 34 | 1 | $6 \times 10^{-11}$ | 1 |
| 17 | $2.3 \times 10^9$ | $1.4 \times 10^{-1}$ | $4.3 \times 10^{-10}$ | | | | |

These results show clearly that the probability of obtaining any line with a specified number of favorable alleles diminishes rapidly as the number of favorable alleles in the resulting progenies increases. While no estimate of the number of favorable alleles were isolated in the genotype of CG00766 can be reasonably made, since the effects of the RFLP markers studied are unknown, the results in Tables 2a, 2b, and 4a through 4h show an unmistakable advantage in favor of CG00766 for many desirable characteristics.

Inbred seeds of CG00766 have been placed on deposit at the American Type Culture Collection (ATCC), Rockville, Md., 20852, under deposit accession number 97060, on Feb. 15, 1995, pursuant to the Budapest Treaty Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An inbred corn line designated CG00766 (ATCC Designation 97060).

2. A plant of the inbred corn line designated CG00766 of claim 1.

3. Plant parts of the plant of claim 2.

4. The plant parts of claim 3 wherein the parts are pollen or a seed.

5. A tissue culture of regenerable cells of inbred corn plant CG00766 (ATCC Designation 97060).

6. A tissue culture according to claim 5 comprising regenerable cells of the plant selected from meristematic tissue, anthers, leaves, embryos, pollen, and protoplasts therefrom.

7. A corn plant regenerated from the regenerable cells of a tissue culture of CG00766 having all of the physiological and morphological characteristics of inbred corn plant CG00766 (ATCC Designation 97060).

8. A method for producing corn seed comprising crossing a first parent corn plant with a second parent corn plant wherein said first or second parent corn plant is the inbred corn plant having designation CG00766 (ATCC Designation 97060) and harvesting the seed resulting from said cross.

9. The method of claim 8, wherein said fast and second parent corn plants are both from the inbred corn line designated CG00766.

10. A first generation ($F_1$) corn plant and seed thereof produced by growing said corn seed of claim 8.

11. A first generation ($F_1$) corn plant and seed thereof produced by growing said corn seed of claim 9.

12. A first generation ($F_1$) hybrid corn plant and seed thereof produced by crossing a first inbred female corn plant with a second inbred male corn plant, wherein said first or second parent corn plant is the inbred corn plant having the designation CG00766 (ATCC Designation 97060), and harvesting the seed of said first inbred female corn plant.

13. The hybrid corn plant and seed thereof of claim 12, wherein said inbred corn plant having the designation CG00766 is the female parent.

14. The hybrid corn plant and seed thereof of claim 12, wherein said inbred corn plant having the designation CG00766 is the male parent.

15. A method for producing first generation ($F_1$) hybrid corn seed comprising crossing a first inbred parent corn plant with a second inbred parent corn plant, wherein said first or second parent corn plant is the inbred corn plant having the designation CG00766 (ATCC Designation 97060), and harvesting the $F_1$ hybrid seed resulting from the cross.

16. A first generation ($F_1$) hybrid corn plant and seed thereof produced by growing said hybrid corn seed of claim 15.

* * * * *